US009366577B2

(12) United States Patent
Kallendrusch et al.

(10) Patent No.: US 9,366,577 B2
(45) Date of Patent: Jun. 14, 2016

(54) COUPLING DEVICE FOR CONNECTING AN OPTICAL WAVEGUIDE TO AN ASSOCIATED OPTICAL WAVEGUIDE CONNECTION

(75) Inventors: Jan Kallendrusch, Koeln (DE); Volker Sinhoff, Wurselen (DE); Christian Wessling, Stolberg (DE); Kai Ulf Markus, Eschweiler (DE)

(73) Assignees: Ingeneric GmbH, Aachen (DE); Vimecon GmbH, Herzogenrath (DE)

( * ) Notice: Subject to any disclaimer, the term of this patent is extended or adjusted under 35 U.S.C. 154(b) by 59 days.

(21) Appl. No.: 14/117,974

(22) PCT Filed: Apr. 12, 2012

(86) PCT No.: PCT/EP2012/056683
§ 371 (c)(1),
(2), (4) Date: Feb. 20, 2014

(87) PCT Pub. No.: WO2012/156155
PCT Pub. Date: Nov. 22, 2012

(65) Prior Publication Data
US 2014/0158872 A1 Jun. 12, 2014

(30) Foreign Application Priority Data
May 19, 2011 (DE) .......... 10 2011 102 079

(51) Int. Cl.
*G01J 1/32* (2006.01)
*G01J 1/04* (2006.01)
(Continued)

(52) U.S. Cl.
CPC ............ *G01K 11/12* (2013.01); *A61B 18/22* (2013.01); *G02B 6/262* (2013.01); *G02B 6/29361* (2013.01); *G02B 6/3845* (2013.01);
(Continued)

(58) Field of Classification Search
CPC .............. G01K 11/12; G02B 6/262; G02B 2006/12135; G02B 2006/12138
USPC ............... 250/227.23, 216, 227.11, 250/227.14–227.2, 227.21, 227.24, 227.27, 250/227.28, 221; 385/31, 154, 8, 9, 12, 27, 385/39
See application file for complete search history.

(56) References Cited

U.S. PATENT DOCUMENTS 3,953,727 A   4/1976 d'Auria et al.
4,994,059 A * 2/1991 Kosa et al. .............. 606/12
(Continued)

FOREIGN PATENT DOCUMENTS

DE     10112455 A1    2/2002
EP     0212786   *   3/1987 ............. A61B 17/36
(Continued)

OTHER PUBLICATIONS

Haishan Zeng, Harvey Lui and David I. McLean, "Skin cancer detection using in vivo Raman spectroscopy", May 11, 2011, SPIE Newsroom DOI: 10.1117/2.1201104.003705.*

*Primary Examiner* — Pascal M Bui Pho
(74) *Attorney, Agent, or Firm* — The Webb Law Firm

(57) ABSTRACT

A coupling device for an optical waveguide includes an optical waveguide connection for a first optical waveguide. The coupling device includes an optical filter arranged in a beam path between a laser light source and the optical waveguide connection which reflects light of a first wavelength range or a first polarization direction and transmits light of a second wavelength range or a second polarization direction.

8 Claims, 4 Drawing Sheets

(51) Int. Cl.
*G01K 11/12* (2006.01)
*A61B 18/22* (2006.01)
*G02B 6/293* (2006.01)
*G02B 6/38* (2006.01)
*G02B 6/26* (2006.01)
*A61B 18/24* (2006.01)
*A61B 19/00* (2006.01)
*A61B 18/00* (2006.01)

(52) U.S. Cl.
CPC ............... *A61B 18/24* (2013.01); *A61B 19/40* (2013.01); *A61B 2018/00172* (2013.01)

(56) References Cited

U.S. PATENT DOCUMENTS

| | | | |
|---|---|---|---|
| 5,098,427 A * | 3/1992 | Hessel et al. | 606/11 |
| 5,154,707 A * | 10/1992 | Rink et al. | 606/12 |
| 5,611,006 A | 3/1997 | Tabuchi | |
| 6,406,196 B1 | 6/2002 | Uno et al. | |
| 6,563,976 B1 | 5/2003 | Grann et al. | |
| 6,618,516 B1 | 9/2003 | Huang | |
| 6,985,647 B2 | 1/2006 | Takamori | |
| 2001/0014193 A1 | 8/2001 | Shibuya | |
| 2002/0064191 A1 | 5/2002 | Capewell et al. | |
| 2003/0216720 A1 | 11/2003 | Sinofsky | |
| 2006/0280411 A1 | 12/2006 | Nishizawa et al. | |

FOREIGN PATENT DOCUMENTS

| | | |
|---|---|---|
| EP | 1014125 A2 | 6/2000 |
| GB | 2332318 A | 6/1999 |
| JP | 59-029219 | 2/1984 |
| JP | 60-156034 | 8/1985 |
| JP | 774343 A | 3/1995 |
| JP | 2004233484 A | 8/2004 |
| JP | 2008104791 A | 5/2008 |
| WO | 9706458 A1 | 2/1997 |
| WO | 2010037374 A1 | 4/2010 |

* cited by examiner

COUPLING DEVICE FOR CONNECTING AN OPTICAL WAVEGUIDE TO AN ASSOCIATED OPTICAL WAVEGUIDE CONNECTION

CROSS-REFERENCE TO RELATED APPLICATIONS

This application is the United States national phase of International Application No. PCT/EP2012/056683 filed Apr. 12, 2012, and claims priority to German Patent Application No. 10 2011 102 079.2, filed May 19, 2011, the disclosures of which are hereby incorporated by reference in their entirety.

BACKGROUND OF THE INVENTION

1. Field of the Invention

The invention refers to a coupling device for connecting an optical waveguide to the associated optical waveguide connection.

2. Description of Related Art

A coupling device couples the light generated by a laser light source into an optical waveguide for further use. The optical waveguide may be a part of a catheter or a medical product, for example, intended to introduce the laser light into the body of a human being or an animal for therapeutic or diagnostic purposes. As an alternative, the optical waveguide could also be used in material processing or for information transmission in the field of telecommunications and information technology. Especially when used as a catheter in medical technology, there is a substantial risk of an overheating of the optical waveguide. With a defective or soiled optical waveguide, the laser radiation is absorbed in the cladding surrounding the optical waveguide fibers and/or at the breaking point of the core. Thereby, the fiber is heated. This heating can cause the fiber material to melt or even evaporate. Specifically as a result of fiber breakage, the increased laser light absorption, e.g. in the case of a cardiac catheter surrounded by liquid, can lead to the formation of plasma with temperatures up to 1,000° C. Especially with cardiac catheters patients run a 50% risk of death due to the plasma formed in the event of overheating. Overheating of optical waveguides can be a typical consequence of a break of light guiding fibers.

SUMMARY OF THE INVENTION

It is an object of the invention to detect the overheating of an optical waveguide within a predetermined period of time.

According thereto, the coupling device comprises a refractive or diffractive filter arranged in the beam path between the laser light source and the optical waveguide connection, the filter reflecting light of a first wavelength range or a first polarization direction and transmitting light of a second wavelength range or a second polarization direction. The reflection or transmission of light is effected at the optical filter in dependence on the wavelength or the polarization. Thus, in the coupling device, heat radiation generated when an optical waveguide becomes overheated or the white light in the wavelength range of visible light, generated in case of plasma, can be guided by the filter along a beam path that is different from the beam path of the laser light. Therefore, a basic idea of the invention provides for a wavelength- and/or polarization-dependent separation of the beam paths of the laser light and of the heat radiation/white light (referred to hereinafter as signal radiation) so as to be able to detect the radiation generated in the event of waveguide overheating separately and to recognize it as an indication of waveguide overheating.

The optical filter may be designed as a dielectric mirror and reflects the laser light onto the optical waveguide connection at an angle of 90°, for example, whereas the signal radiation generated during overheating and reflected onto the optical filter by the waveguide is transmitted through the optical filter and is detected on the side of the optical filter opposite the optical waveguide connection. As an alternative, the optical filter can be designed such that the laser light is transmitted from the laser light source through the optical filter to the opposite optical waveguide connection, whereas reflected signal radiation is reflected from the optical waveguide connection at the mirror, e.g. under an angle of 90°. The optical filter performs a wavelength- or polarization-dependent reflection and transmission in order to separate, in the coupling device, the beam path of the light coupled into the optical waveguide from the beam path of the signal radiation reflected in case of waveguide overheating, so that reflected signal radiation can be detected separately as an indication of waveguide overheating.

As an alternative, the optical filter may be designed as a diffractive reflection or transmission grid or dispersion prism that diffracts or refracts the radiation reflected from the waveguide in different directions, depending on the wavelength, polarization and angle of incidence, so that the signal radiation can be resolved spectrally by a spatial separation of a plurality of detectors. Preferably, a first light meter means is arranged in a beam path extending from the optical waveguide connection via the optical filter to the first light meter means, so that the reflected signal radiation generated in case of overheating can be measured by the first light meter means. Preferably, the first meter means is arranged on the side of the optical waveguide connection opposite the optical filter, the optical filter transmitting the reflected signal radiation and reflects the laser light from the laser light source to the optical waveguide connection.

As an alternative or in addition, a second light meter means can be arranged in a beam path from the laser light source via the optical filter to the second meter means in order to be able to detect overheating or cable breakage also in a waveguide between the laser light source and the optical filter. Here, the first meter means and/or the second meter means should each be designed to measure the output of light in either the first or the second wavelength range in order to measure, for example, only the signal radiation in the event of fiber overheating, without detecting noise parts of the laser light that would compromise the measuring result.

The first and/or the second meter means preferably comprise a photodiode with an optical filter in the beam path between the photodiode and the optical filter, the optical filter only allowing light of the one wavelength range to pass and blocking light of the other wavelength range. As an alternative, the meter means can also be a detector cell with a plurality of optical sensors arranged in a row.

The first wavelength range reflected by the optical filter preferably comprises a wavelength range of at least one laser light source outside of the range of visible light, so that only the laser light, but no visible signal radiation, is reflected by the optical filter. The first wavelength range may be within the infrared range beyond 800 nm, whereas the second wavelength range is the wavelength range of visible light, in particular below 800 nm. Thus, the optical filter transmits only the signal radiation in the form of white light that is generated in the event of overheating caused by fiber breakage, whereas the laser light from the laser light source is not transmitted.

The transmitted signal radiation is detected by one of the meter means. Upon the detection of signal radiation by one of the meter means, an emergency stop function can be activated that allows a deactivation of the laser light source within a period of a few milliseconds when the waveguide overheats, so that health risks for a patient are avoided.

The optical filter can reflect a part of the light output of the first wavelength range, i.e. of the laser light, and can transmit a part of this light output. For example, the reflected laser light part can be directed from the laser light source to the optical waveguide connection, whereas the other part is transmitted towards one of the two meter means in order to immediately detect damage to the feeding beam path between the laser light source and the optical filter from the measured light output.

Besides the optical waveguide connection, the coupling device preferably further comprises a waveguide input to which a second optical waveguide can be connected in order to supply the laser light of an external laser source to the coupling device.

Bundling optics for bundling laser light or signal radiation can be provided between the second waveguide and the optical filter, between the optical filter and the first waveguide, between the optical filter and the first meter means and/or between the optical filter and the second meter means.

BRIEF DESCRIPTION OF THE DRAWINGS

The following is a detailed explanation of embodiments of the invention with reference to the drawings.

In the Figures.

DESCRIPTION OF THE INVENTION

Figure 1:
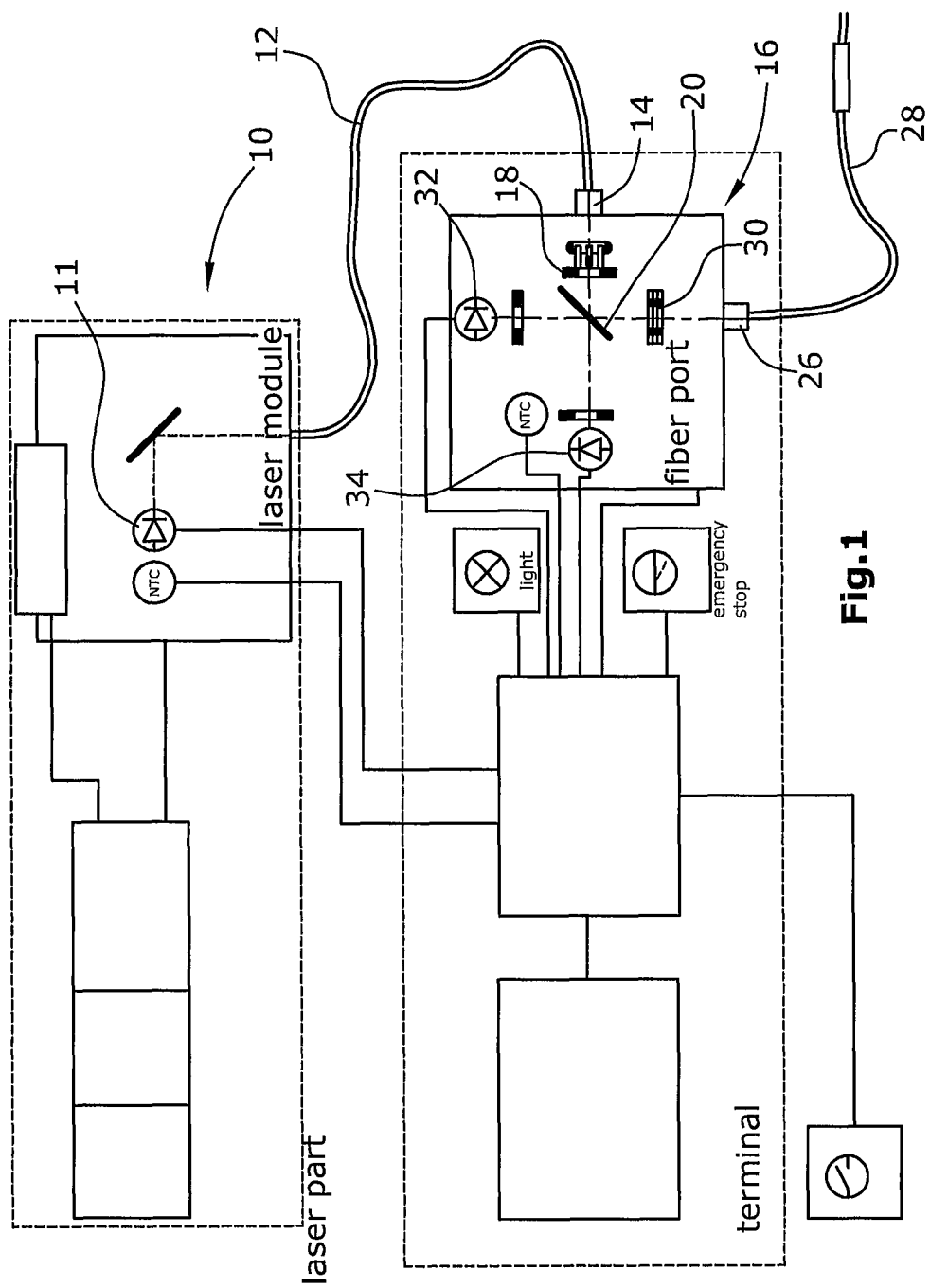
FIG. 1 is a schematical illustration of a first embodiment.

FIG. 1 illustrates a laser device 10 of conventional design comprising a laser light source 11 in the form of a laser diode for generating laser light. The laser light has a working wavelength of about 980 nm that is outside the wavelength range of visible light of 380-780 nm. The laser light generated is coupled into a second optical waveguide 12 and is coupled into the coupling device 16 of the invention via the waveguide inlet 14. The laser light coupled in is directed onto the optical filter 20 through bundling optics 18, which filter is arranged in the beam path from the waveguide inlet 14 to the optical filter 20 under an inclination of about 45° relative to the propagation of the laser light.

The optical filter 20 reflects light in a first wavelength range 22 of more than 850 nm, whereas light of the second wavelength range 24, which is less than 850 nm, is transmitted. Thus, the laser light coupled in, having a wavelength of 980 nm, is reflected by the optical filter by 90° towards the optical waveguide connection 26 and is coupled into the first optical waveguide 28 via the optical waveguide connection 26. The optical waveguide 28 is a laser cardiac catheter for application in cardiology in order to direct laser light with typical outputs of about 40 W to affected regions of the heart muscle for the treatment of cardiac insufficiency or disturbances of the heart muscle or the rhythm of the heart. In the event of a waveguide breakage or a breakage of a plurality of fibers of the waveguide, the energy is converted into heat at the breakage site. When used in a blood-filled heart or in the vascular system of a patient, the resulting temperature of up to 1,000° C. and beyond causes plasma to form which generates a signal radiation in the form of white light. The differentiation between laser light and signal radiation (white light) is based exclusively in dependence on the wavelength or, if applicable, in dependence on the polarization and is thus independent of output. Thereby, it is also possible to detect signal radiation with a significantly lower output with respect to laser light, which signal radiation is returned through the optical waveguide 28 to the optical waveguide connection 26.

The white light reflected by the optical waveguide connection 26 is directed through the bundling optics 30 between the optical waveguide connection 26 and the optical filter 20 to the optical filter 20 and is not reflected onto the waveguide inlet 14 by the same, but is transmitted towards the first meter means 32. The white light is transmitted and not reflected, because its wavelengths of a maximum of 780 nm fall into the second wavelength range 24 below 850 nm that is transmitted by the mirror 20, but not reflected. The first meter means 32 is arranged on the side of the optical waveguide connection 26 opposite the optical filter 20 such that a beam path follows a straight course from the optical waveguide connection 26 through the optical filter 20 to the photodiode of the first meter means 32.

The first meter means 32 is further provided with an optical filter between the optical filter 20 and the photodiode of the meter means 32. The optical filter is a band pass filter with a passband in the range of visible light so that possible laser light with a wavelength of more than 900 nm does not reach the photodiode.

A second light meter means 34 is arranged on the side of the optical waveguide inlet 14 opposite the filter 20 such that light from the optical waveguide inlet 14 impinges on the photodiode of the second meter means 34 via the optical filter 20. Thus, white light which, due to a breakage in the in-coupling second optical waveguide 12, impinges on the optical waveguide inlet 14 can be transmitted through the optical filter 20 and be measured by the photodiode of the second meter means 34. Moreover, the optical filter 20 is designed such that about 99.99% of the laser light of the first wavelength range 22 are reflected and about 0.01% of the output are transmitted. Thus, in normal operation with undamaged second waveguide 12, the second meter means 34 detects 0.01% of the laser output. If the laser light output differs significantly from 0.01%, because too little laser light reaches the coupling device 10, e. g. because of a waveguide breakage or fissure or a malfunction of the laser light source 11, or because, due to a malfunction of the laser light source 11, the laser light output coupled in is exceeded to an extent dangerous for a patient, the measuring signal can activate an emergency stop function for the deactivation of the laser source.

Figure 2:
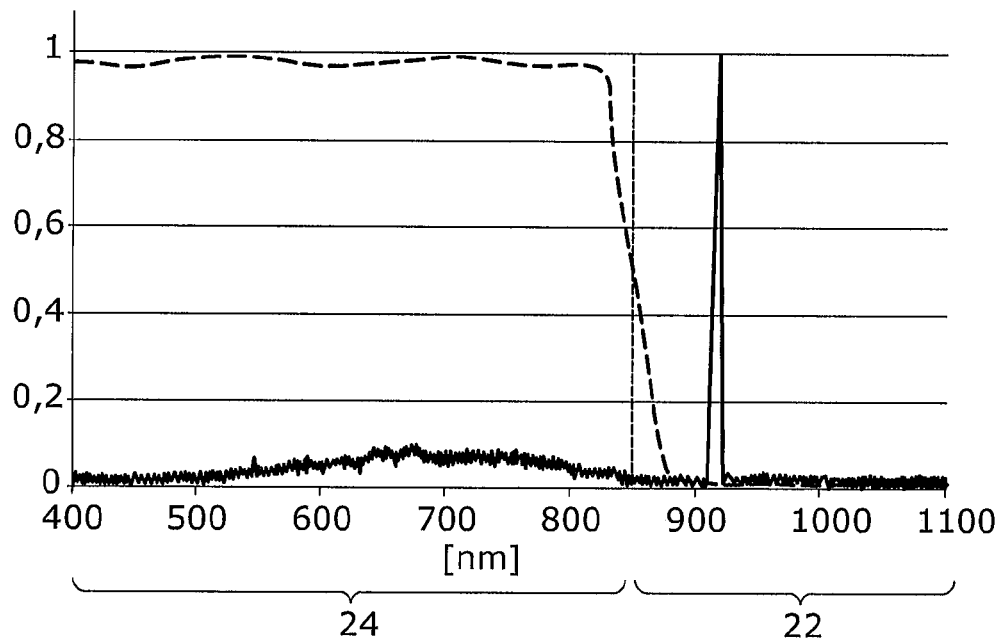
FIG. 2 is a diagram including the wavelength components of the first and the second wavelength range.

FIG. 2 illustrates the two wavelength ranges 22 and 24 separated from each other by the optical filter 20. The laser light generated by the laser light source 11 has a maximum, standardized to the value 1, in the range of the working wavelength of the laser of 980 nm. As is exemplified by the transmission curve of the optical filter 20 (illustrated by the broken line), the laser light with the working wavelength of 980 nm is not transmitted, but is reflected. In the second wavelength range 24, a further local maximum in the range between 670 nm and 750 nm can be seen. The wavelength component results from the signal radiation in the range of visible light (white light) caused by a damage to the waveguide 28. This wavelength component of the signal radiation is transmitted almost completely by the optical filter 20, but is not reflected, as is represented by the overlap with the broken line for the transmitted wavelength components in FIG. 2.

Figure 3:
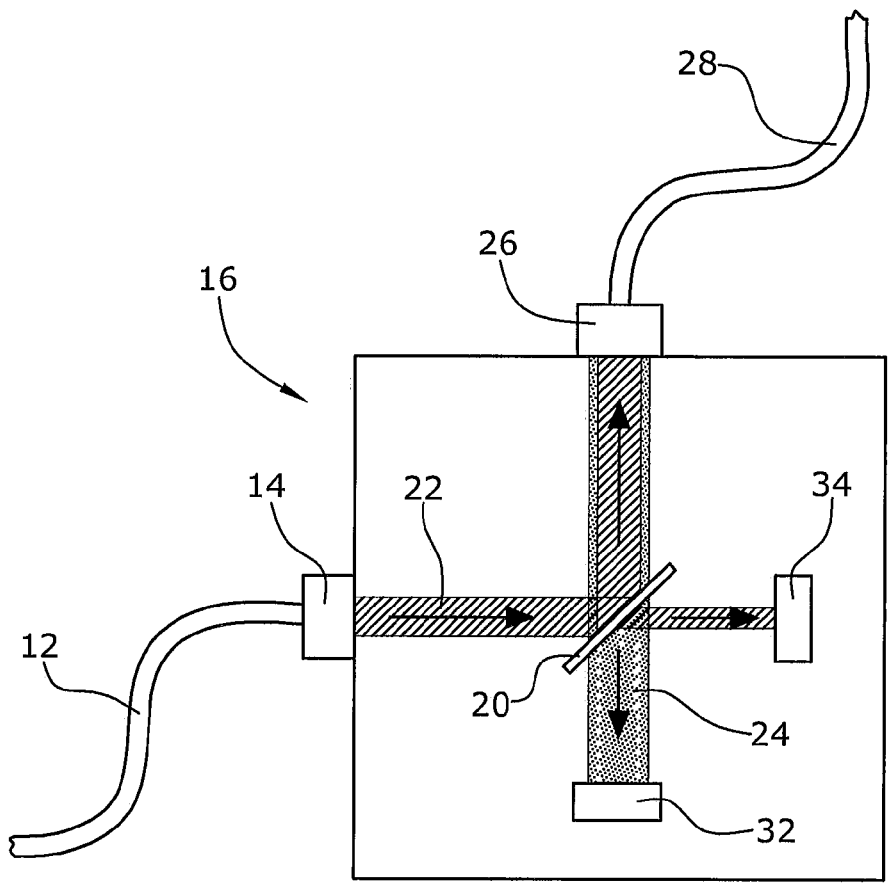
FIG. 3 is a simplified illustration of the first embodiment.

FIG. 3 is a simplified illustration of the basic principle of the first embodiment, wherein the laser light (shown as hatched lines) is reflected for the greater part from the optical waveguide inlet 14 to the optical waveguide connection 26 and is transmitted for a smaller part towards the second meter means 34. The optical filter 20 transmits the signal radiation (shown as dots), which is reflected in the optical waveguide 28, from the optical waveguide connection 26 completely towards the first meter means 32.

Figure 4:
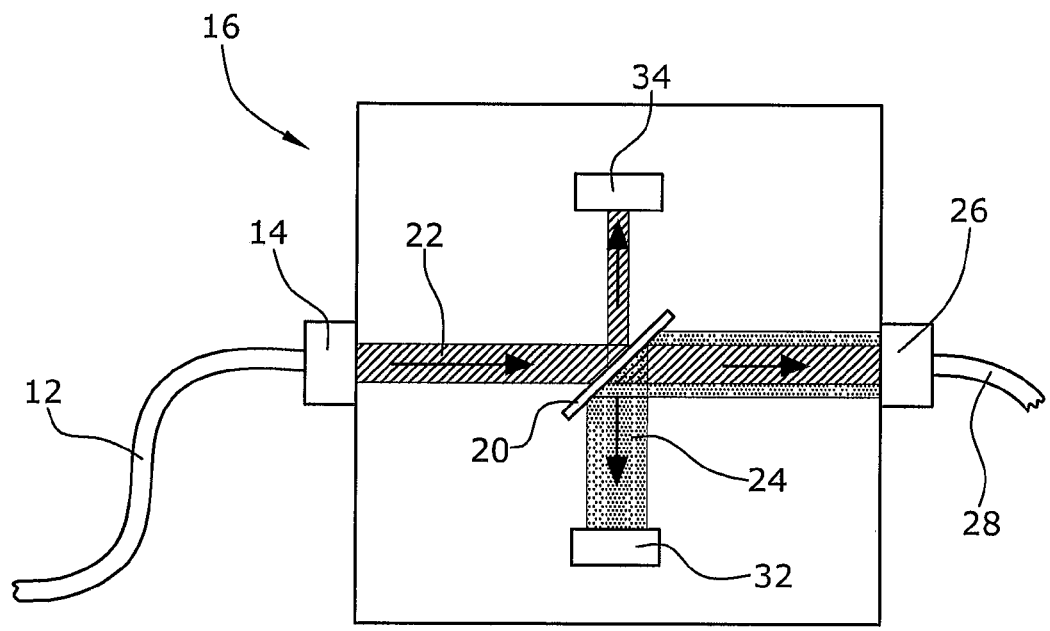
FIG. 4 shows a second embodiment in correspondence with the illustration in FIG. 3.

The second embodiment illustrated in FIG. 4 differs from the first embodiment in FIG. 3 in that the optical waveguide inlet 14 and the optical waveguide connection 26 are arranged along a straight path on opposite sides of the optical filter 20, wherein a major part of the light of the first wavelength range 22 (laser light) is transmitted through the optical filter 20 towards the optical waveguide connection 26, while a lesser part of the light output in the first wavelength range 22 is reflected by the optical filter 20 towards the second meter means 34. The signal radiation (shown as dots) reflected in the optical waveguide 28 is reflected completely at the optical filter 20 from the optical waveguide connection 26 to the first meter means 32.

Figure 5:
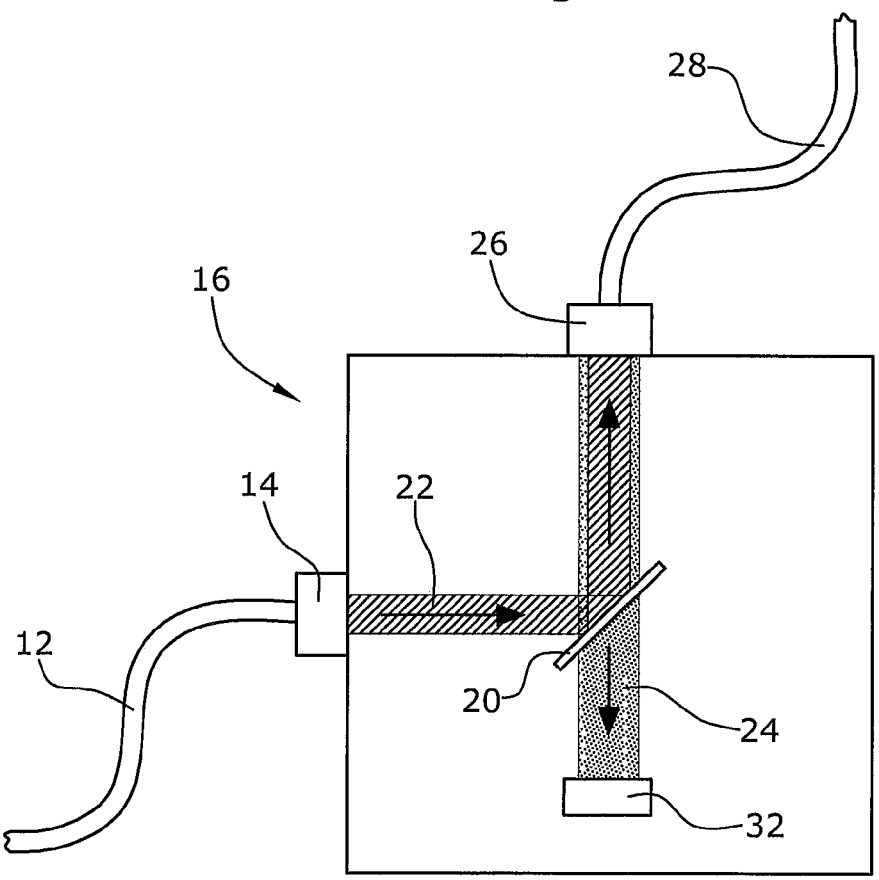
FIG. 5 shows a third embodiment in correspondence with the illustration in FIG. 3.

The third embodiment illustrated in FIG. 5 differs from the first embodiment in FIG. 3 in that the light output of the first wavelength range 22 is reflected completely at the optical filter 20 from the optical waveguide inlet 14 towards the optical waveguide connection 26 without a part thereof being transmitted. No first meter means 32 is provided.

Figure 6:
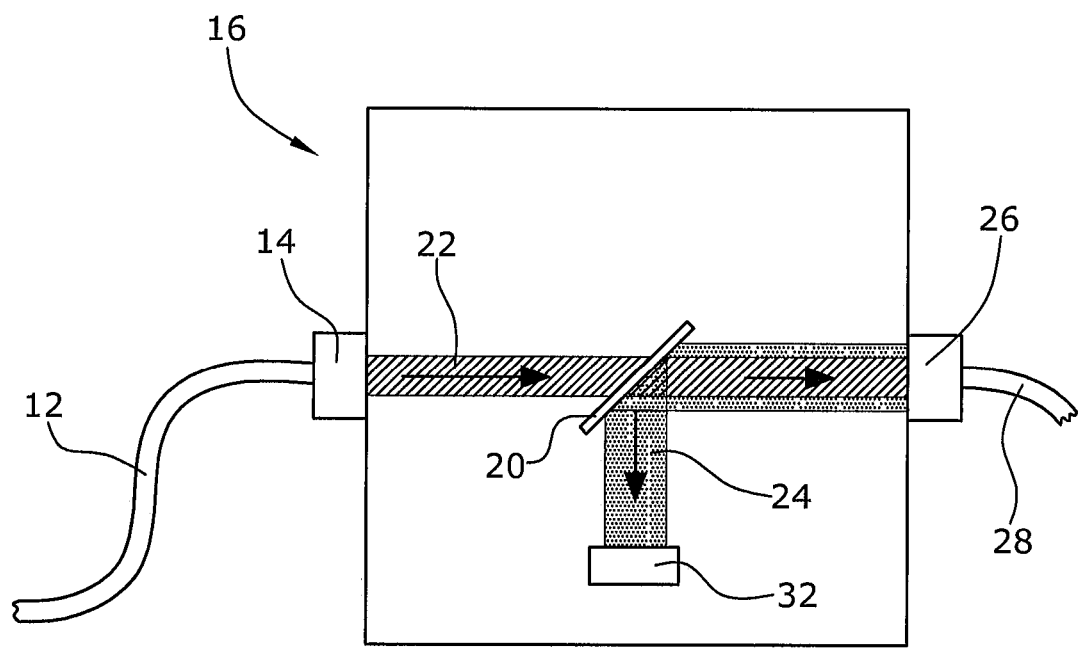
FIG. 6 shows a fourth embodiment in correspondence with the illustration in FIG. 3.
Figure 7:
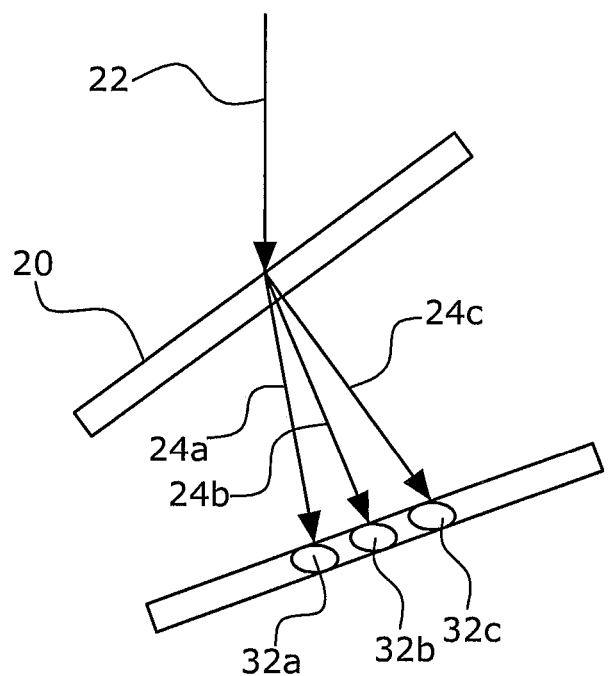
FIG. 7 illustrates a detail of another embodiment.

The fourth embodiment illustrated in FIG. 6 differs from the second embodiment illustrated in FIG. 4 in that the light output of the first wavelength range 22 (laser light) is transmitted in its entirety from the optical waveguide inlet 14 through the optical filter 20 in the direction of the optical waveguide connection 26 without a part of the light output of the first wavelength range 22 being reflected. No second light meter means 34 is provided.

Complementary to FIGS. 1 to 6, FIG. 7 describes an arrangement comprising a diffractive optical filter 20, wherein the signal light 22 is decomposed spectrally into different partial beams 24a, 24b, 24c by diffraction and is distributed to the light meter means 32a, 32b, 32c.

The invention claimed is:

1. A coupling device for an optical waveguide comprising:
an optical waveguide connection for a first optical waveguide;
an optical filter arranged in a beam path between a laser light source and the optical waveguide connection;
a first light meter arranged such that light reflected by the optical waveguide connection is directed to the optical filter and transmitted to the first light meter; and
a second light meter arranged such that at least a portion of light from the laser light source is transmitted through the optical filter to the second light meter,
wherein the optical filter reflects light of a first wavelength rage or a first polarization direction and transmits light of a second wavelength range or a second polarization direction, and
wherein, if the light meter detects light reflected by the optical waveguide connection indicating an overheating of the first optical waveguide and/or the second light meter detects light outside of a predetermined amount being transmitted from the optical filter indicating a failure in the laser light source, a signal is generated to deactivate the laser light source.

2. The coupling device of claim 1, wherein the first light meter and/or the second light meter are respectively designed to measure the output of light of either the first or the second wavelength range.

3. The coupling device of claim 2, wherein the first light meter and/or the second light meter each comprise a photodiode and a light meter optical filter in the beam path between the photodiode and the optical filter, wherein the light meter optical filter of the first light meter transmits only light of the one of the first or the second wavelength range that the first light meter is designed to measure, and wherein the light meter of the optical filter of the second light meter transmits only light of the one of the first or the second wavelength range that the second light meter is designed to measure.

4. The coupling device of claim 1, wherein the first wavelength range comprises a wavelength range of at least one laser source outside the range of visible light.

5. The coupling device of claim 1, wherein the second wavelength range comprises visible light.

6. The coupling device of claim 1, wherein light bundling optics is provided between the optical filter and the first waveguide, between the optical filter and a second waveguide, between the optical filter and the first light meter and/or between the optical filter and the second light meter.

7. The coupling device of claim 1, wherein the coupling device comprises an optical waveguide inlet for a second optical waveguide, wherein the optical filter is arranged in the beam path between the optical waveguide inlet and the optical waveguide connection.

8. The coupling device of claim 1, wherein the coupling device for the signal light comprises a diffractive or dispersive filter spectrally distributing the signal light to different light meters.

* * * * *